Figure 1:
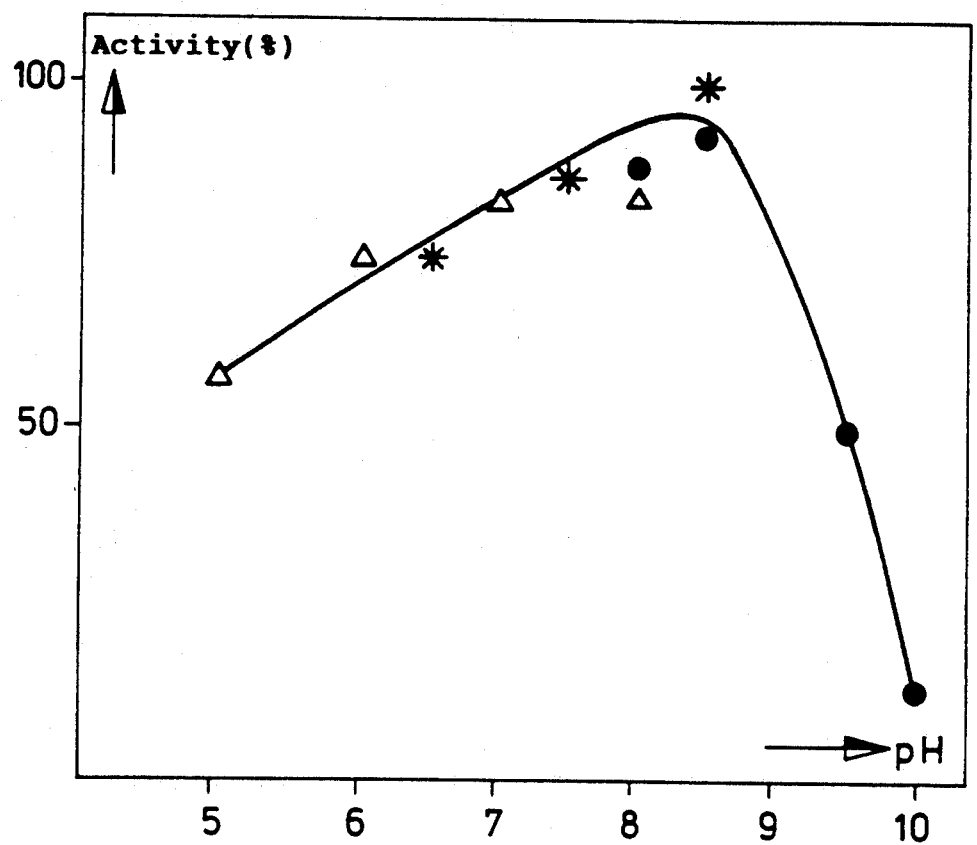

United States Patent [19]
Van Dooren et al.

[11] Patent Number: 5,248,608
[45] Date of Patent: Sep. 28, 1993

[54] PROCESS FOR SEPARATION OF α-SUBSTITUTED CARBOXYLIC ACID AMIDES USING L-AMIDASE FROM *OCHROBACTRUM ANTHROPI*

[75] Inventors: Theodorus J. G. M. Van Dooren, Roermond; Wilhelmus J. J. Van Den Tweel, Meerssen, both of Netherlands

[73] Assignee: DSM N.V., Netherlands

[21] Appl. No.: 819,129

[22] Filed: Jan. 10, 1992

[30] Foreign Application Priority Data

Jan. 11, 1991 [NL] Netherlands .......................... 9100038

[51] Int. Cl.$^5$ ............................................. C12P 13/02
[52] U.S. Cl. ..................................... 435/280; 435/136; 435/822; 435/824
[58] Field of Search ................ 435/280, 136, 822, 824

[56] References Cited

U.S. PATENT DOCUMENTS

| | | | |
|---|---|---|---|
| 4,443,548 | 4/1984 | Oshima et al. | 435/280 |
| 4,481,362 | 11/1984 | Nakai et al. | 548/498 |

FOREIGN PATENT DOCUMENTS

| | | |
|---|---|---|
| 383403 | 8/1990 | European Pat. Off. |
| 3629242 | 3/1987 | Fed. Rep. of Germany |

OTHER PUBLICATIONS

Asano Y, J. Biol Chem 264:14233-9 (1989),
Asano Y, BBRC 162:470-4 (1989),
ATCC Catalog pp. 112-113 (1989).
Chemical abstracts 105 (13), p. 555 Dec. 29, 1986, abstract No. 113629s.
Tetrahedron 45 (No 18, 1989), Pergamon Press (Oxford, GB) Y. Kato et al.: "First stereoselective synthesis of D-amino acid N-alkyl amide catalyzed by D-aminopeptidase"; pp. 5743-5754.

*Primary Examiner*—Douglas W. Robinson
*Assistant Examiner*—S. Saucier
*Attorney, Agent, or Firm*—Cushman, Darby & Cushman

[57] ABSTRACT

Enzyme-catalysed preparation of an α-substituted optically active carboxylic acid, using enantioselective hydrolysis of a mixture of the enantiomers of the corresponding amide, an *Ochrobactrum anthropi* or an *Klebsiella sp.* being used as the enzyme. During the hydrolysis both the L-carboxylic acid and the remaining D-carboxylic acid amide are obtained with high optical purity and high yield, while the activity of the micro-organism is high. A large number of α-substituted carboxylic acid amides with a remarkable structural variety can be hydrolysed in this manner.

7 Claims, 2 Drawing Sheets

PROCESS FOR SEPARATION OF αSUBSTITUTED CARBOXYLIC ACID AMIDES USING L-AMIDASE FROM *OCHROBACTRUM ANTHROPI*

The present invention concerns a process for the preparation of an α-substituted, optically active carboxylic acid, by means of enzyme-catalysed enantioselective hydrolysis of a mixture of the enantiomers of the corresponding amide and isolation of the optically active carboxylic acid.

α-amino acids, both naturally-occurring and synthetic, are important molecules with many applications in the food industry, the pharmaceutical industry, the agrochemical industry, etc. Optically pure D-(−)-phenylglycine is an important building block for the antibiotics ampicillin and cephalexin, while D-(−)-parahydroxyphenylglycine is an intermediate in the preparation of the antibiotic amoxicillin. The naturally-occurring amino acid L-valine is highly suitable as a precursor of cyclosporine-A fermentations, while the D-enantiomer is a valuable intermediate for fluvalinate (insecticide). D- and L-homophenylalanine, as well as synthetic amino acids, can be used as building blocks in the synthesis of various ACE-inhibitors.

Besides α-amino acids, α-alkyl-α-amino acids are also important in various industries. L-α-methyl-3,4-dihydroxyphenylalanine, for example, is an important pharmacon for hypertension.

α-N-hydroxyamino acids and/or derivatives thereof as well as peptides thereof generally have biological activity and usually antibiotic and/or antitumour activity. E. Buehler and G. B. Brown (J. Org. Chem. 32 (1967) 265) state that various N-hydroxyamino acids are constituents of different antibiotics obtained during microbiological fermentations, and these authors list a number of α-N-hydroxyamino acids obtained from naturally-occurring peptides.

Chiral α-hydroxy acids are also important molecules in the production of both pharmaceutical products and agrochemical products: for example α-hydroxypropionic acid (herbicides), α-hydroxyphenyl butyric acid (ACE inhibitors) and mandelic acid (splitting agents). An additional important advantage of the current splitting technology when used with α-hydroxy acids is that optically active α-hydroxy acid amides are left over, which can be reduced to chiral α-hydroxyamines, which are of great interest for the synthesis of β-blockers.

Enzyme-catalyzed, enantioselective hydrolysis of α-hydroxycarboxylic acid amides is described in JP-A-6188894. The process described there uses *Aeromonas hydrophila* (FERM P-7360) and *Moraxella phenylperuvica* (FERM P-7359) The substrates are limited to α-hydroxycarboxylic acid amides.

A disadvantage of this process is that the yield and the optical purity (enantiomeric excess) are relatively low. The optical purity achieved is only 90-95%, whereas, for many applications, particularly pharmaceutical applications, an optical purity of at least 99% is required.

The purpose of this invention is to provide a process by means of which the optically active L-carboxylic acid and also the remaining D-carboxylic acid amides are obtained with an enantiomeric excess (e.e.) of more than 95% more specifically more than 98% and in most cases more than 99% and in which, also, a high yield is achieved.

According to the present invention, this is achieved by hydrolysis of racemic carboxylic acid amides α-substituted with an amino-, hydroxy- or N-hydroxy amine group, the enzyme used being an *Ochrobactrum anthropi* or a Klebsiella sp.

It has been found that, when an *Ochrobactrum anthropi* or a Klebsiella sp. is used, the L-carboxylic acid and the remaining D-carboxylic acid amide are obtained in a highly optically-pure form and with a high yield, while, moreover, the micro-organism has an extremely high activity, which makes its application on a commercial scale possible. It has also been found that using the micro-organism according to this invention, a very large number of α-substituted carboxylic acid amides with a remarkable structural diversity can be hydrolysed with high selectivity and activity. Preferably, *Ochrobactrum anthropi* NCIB 40321 or Klebsiella sp. NCIB 40322 is used.

Examples of suitable substrates are α-aminoacid amides with 2-20 carbon atoms such as phenylglycine amide, para-hydroxyphenylglycine amide, valine amide, etc. Hydrolysis of, for example, α-amino acid amides proceeds rapidly compared with hydrolysis in the presence of known amidases (aminopeptidases) such as those from *Pseudomonas putida*. One advantage is that the hydrolysis activity takes place over a wide pH range. Other suitable substrates are, for example, α-hydroxy acid amides and α-N-hydroxy amino acid amides. The carboxylic acid amides mainly contain 2-20 carbon atoms and can contain a second substitute in the α-position, for example an alkyl group.

The enzymatic hydrolysis of α-N-hydroxy-aminoacid amines has never before been described in literature. One problem with this type of hydrolysis process is that the α-N-hydroxy-aminoacid obtained decarboxylizes under the basic conditions, which are usually applied in such processes. Applicant has now found that in the process according to this invention good activity has also been achieved at low pH values, with no decarboxylation, or scarcely any decarboxylation, occurring. As oxygen acts as a catalyst for the chemical decarboxylization reaction, during hydrolysis of α-N-hydroxy-aminoacid amides the reaction mixture is preferably flushed with molecular nitrogen. The hydrolysis is then carried out under molecular nitrogen.

The present invention is based on an enantioselective enzymatic hydrolysis, wherein there is a very great preference for the L-enantiomer of the substrate to be hydrolysed to the corresponding L-acid and the D-enantiomer to remain a D-amide.

The organisms used in the present process are *Ochrobactrum anthropi* and Klebsiella sp., particularly *Ochrobactrum anthropi* NCIB 40321 and Klebsiella sp. NCIB 40322. The production of these organisms takes place in aerated media which contain components/constituents such as a carbon source, a nitrogen source, vitamins and minerals. In order to optimise the activity and selectivity of this type of enzyme preparation a small amount of the amide to be hydrolysed or another suitable inducer can be added to the culture medium. Cultivation can be carried out in batches, in fed-batches or continuously.

Similar cultivation processes are known from and described in detail in patents and scientific publications, such as, for example, EP-A-244912; a description of the cultivation processes is in this context therefore unnecessary. The enzyme preparation as used in the present invention is not subject to the constraints of purity and suchlike and may be either a crude enzyme solution or a purified enzyme; it may also consist of permeabilised cells which have the required activity, or of a homogenate of cells with a similar activity. The enzyme can also be used in immobilized form or in a chemically modified form. The invention is in no way limited by the form in which the enzyme is used for the present invention. Within the context of the invention an enzyme derived from a mutant or from a genetically modified microorganism can of course also be used.

Enantioselective enzymatic hydrolysis is known as such. The enantioselectivity is based on a difference in the conversion speed of the various enantiomers. It has been found that in the present process almost exclusively one enantiomer of the amide is hydrolysed, resulting in a conversion of approximately 50% and an e.e. product and an e.e. substrate of approximately 100%. An additional advantage of the process according to the invention is that the remaining substrate, the D-enantiomer of the carboxylic acid amide, can also be recovered. Using a known process, for example non-stereospecific enzymes, this carboxylic acid amide can subsequently be hydrolysed to the other enantiomer of the carboxylic acid. The relationship between conversion and e.e. value is described for enantioselective enzymatic hydrolyses by Qu-Ming Gu et al. in Tetrahedron Letters 27 (1986) 5203ff. and in more general terms by Ghing-Shih Chen et al. in J. Am. Chem. Soc. 104 (1982) 7294ff. The general theory regarding enantioselective conversions described in these publications also applies to the present process.

The cells used in the reaction can be separated off if desired and re-used in a subsequent conversion without the activity being appreciably affected.

The hydrolysis can be carried out by adding the amide to the culture medium at the start of, during or after the cultivation of the micro-organism in question. Cultivated cells can also be harvested, for example by centrifugation, and added to the reaction medium containing the amide. In this case both cell suspensions and dried cells can be used, for example lyophilized cells, spray-dried cells, and cells treated with an organic solvent, such as acetone or toluene. Destroyed cells or extracts from cells can also be used.

The reactions are usually carried out in an aqueous environment. It is also possible to carry out these hydrolysis reactions in the presence of organic solvents.

The reaction conditions for the hydrolysis are not too critical. The reaction is usually carried out in an aqueous environment, but mixtures of water and organic solvents can also be used. The pH is set using, for example, KOH, NaOH or $NH_4OH$ to a value within the activity range of the enzyme; this is usually from 3 to 11 and preferably from 4 to 9.5. Moreover, the hydrolysis is usually carried out at an ambient, or slightly higher, temperature, i.e. between 20° C. and 85° C. A temperature of between 30° C. and 70 ° C. is preferred. Obviously the reaction conditions should be chosen in such a way as to avoid any inconvenient side reactions.

The concentration of the substrate can vary within wide limits and can be, for example, from 2.5 to 500 g/l. In order to avoid side reactions with the substrate or the product the conversion can take place in the absence of oxygen, for example by flushing with molecular nitrogen.

It has been found that, using the method according to the present invention, and using the micro-organisms described above, a large number of α-substituted carboxylic acid amides can be hydrolysed to the corresponding carboxylic acid with very high selectivity and activity. In practice it is particularly advantageous to use the same biocatalyst for the preparation of different products as these particular products usually each represent only a small sales volume.

The invention will be further illustrated by reference to the following examples, without, however, being limited to these.

In these examples the analyses of the reaction products, especially the determination of the enantiomeric excess (e.e.), were carried out using two HPLC methods, in which, if desired, the selectivity value of the reaction can be calculated using the formulae of Ghing-Shih Chen et al. (J. Am. Chem. Soc. 104 (1982) 7294 ff). Both the α-H-α-amino acids and the α-alkyl-α-amino acids and the corresponding amino acid amides were analysed as described by A. Duchateau et al. (J. Chromatogr. 471 (1989) 263). The enantiomer composition of mandelic acid was determined by separating both enantiomers on a reversed phase column (Nucleosil 120-$C_{18}$) using ligand-exchange chromatography. The eluent used was prepared as follows: 0.2 g triethylamine was added to 1,800 ml of $H_2O$ in a 2 l volumetric flask; then 0.8 g $Cu(CH_3COO)_2.2H_2O$ and 1.38 g N,N-di-n-propyl-L-alanine were added. The pH was set to 5.3 using acetic acid (1.8 mol/l) and then the volumetric flask was topped up to 2 liters with $H_2O$. The solution obtained was filtered through a Sartorius membrane filter (0.45 μm) and mixed with acetonitrile in the following ratio: 230 Cu-solution/ 20 acetonitrile (v/v). The flow rate was 1.5 ml/min, and the temperature was 40° C. The components were selectively detected using a post-column reaction with a $Fe_2(SO_4)_3$ reagent (500 mg $Fe_2(SO_4)_3.nH_2O$ in 600 ml of $H_2O$; pH set at 2.1 using $H_2SO_4/H_2O$ (10/240-solution). Detection was carried out with an UV-vis detector at 420 nm. For the determination of the conversion, the above-mentioned HPLC methods were used, either a reversed phase HPLC system with UV detection or an ion-selective ammonia electrode with which the ammonia released during the hydrolysis reaction was measured.

Example I

Cultivation of the biocatalyst

Cultivation of *Ochrobactrum anthropi* NCIB 40321 and *Klebsiella* sp. NCIB 40322 took place in 2 l Erlenmeyer flasks filled with 500 ml of medium, which, while being stirred (150 rpm), were incubated at 28° C. The medium contained the following components: 10 g/l yeast carbon base (Difco), 1.5 g/l DL-mandelic acid amide, and 50 mM potassium phosphate buffer pH 7.0. Approximately twenty hours after inoculation the cultivated cells were harvested by centrifugation (10 min, 15,000 g), washed using a potassium phosphate buffer (50 mM, pH 7.0) and resuspended in the same buffer. The cell suspension thus obtained was either used direct for enzymatic hydrolysis or first deep-frozen for a short time (−20 ° C).

Example II

Hydrolysis of DL-phenylglycine amide.

*Ochrobactrum anthropi* NCIB 40321 was cultivated as described in example I.

The cell suspension thus obtained contained 50 mg dry weight per ml. 0.5 ml of this cell suspension was added to 19.5 ml of 100 mM potassium phosphate buffer pH 8.0 which contained 5.0 g/l DL-phenylglycine amide. After 15 min. incubation (40° C., 150 rpm), 50% of the added amide was hydrolysed. HPLC analyses showed that only the L-amide was hydrolysed. The remaining reaction mixture contained both L-phenylglycine and D-phenylglycine amide with an e.e. ≧99.5%. During incubation with L- and D-phenylglycine amide separately only the L-phenylglycine amide was hydrolysed. Ammonia accumulated in stoichiometric amounts.

Example III

The enantioselective hydrolysis of DL-mandelic acid amide

*Ochrobactrum anthropi* NCIB 40321 and *Klebsiella sp.* NCIB 40322 were cultivated as described in example I. As in example 2, the cell suspension of Ochrobactrum obtained contained 50 mg dry weight/ml and the Klebsiella cells 48 mg dry weight/ml. 2.0 ml of these cell suspensions were added to 18 ml of 100 mM potassium phosphate buffer pH 7.0 which contained 1.0 g/l DL-mandelic acid amide. After 70 min. incubation (28° C., 150 rpm) the incubation was stopped and the reaction mixture analysed. The conversion was determined with both HPLC and the ion-selective ammonia electrode. The results are given in table 1.

TABLE 1

| | Conversion | | | E | |
|---|---|---|---|---|---|
| | $NH_3$ | HPLC | e.e.$_p$ | $NH_3$ | HPLC |
| Ochrobactrum anthropi NCIB 40321 | 0.48 | 0.46 | 98.4% | 378 | 330 |
| Klebsiella sp. NCIB 40322 | 0.32 | 0.40 | 97.1% | 107 | 133 |

Example IV

Hydrolysis rate as a function of pH

In the same way as in example III, using *Ochrobactrum anthropi* NCIB 40321 cells, the hydrolysis activity of DL-mandelic acid amide was examined as a function of the pH. The incubation was carried out at 60° C. The following buffers (100 mM) were used: potassium phosphate buffer (Δ); Tris/HCl buffer (*), glycine/NaOH buffer ( ). The results are given in FIG. 1. An activity of 100% to a hydrolysis rate of 140 nmol min$^{-1}$ (mg dry weight)$^{-1}$.

Example V

Hydrolysis rate as a function of temperature

Figure 2:
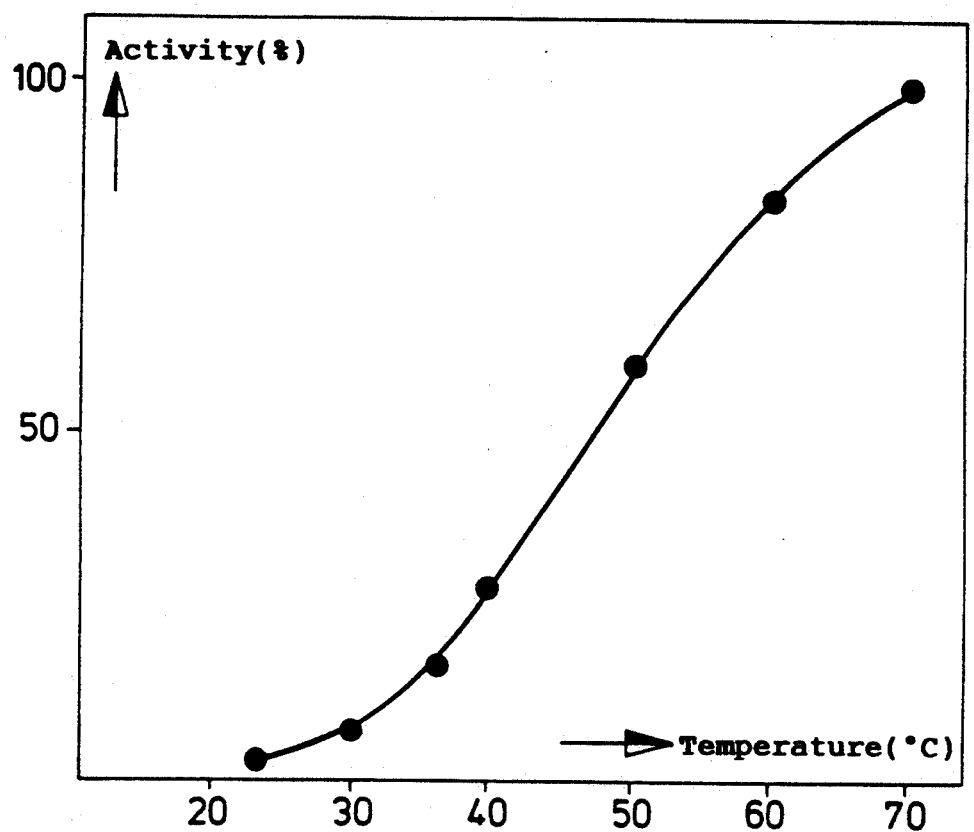

In the same way as in example III, using *Ochrobactrum anthropi* NCIB 40321 cells, the hydrolysis activity of DL-mandelic acid amide was examined as a function of the temperature. The incubation was carried out at pH 8.5 (100 mM Tris/HCl). The results are given in FIG. 2. An activity of 100% corresponds to a hydrolysis rate of 175 nmol min$^{-1}$ (mg dry weight)$^{-1}$.

Example VI

Substrate and/or product inhibition

In the same way as in example III using *Ochrobactrum anthropi* NCIB 40321 cells, the hydrolysis activity of DL-mandelic acid amide was examined as a function of both the mandelic acid amide and the mandelic acid concentration. In the presence of 100 g/l mandelic acid the activity was virtually the same as the activity measured in example 3. In the presence of 100 g/l mandelic acid amide the activity was 25% lower than the activity measured in example 3.

Example VII

The enantioselective hydrolysis of α-N-hydroxyphenylglycine amide

In the same way as in example I, *Ochrobactrum anthropi* NCIB 40321 was cultivated. 19.5 ml of 100 mM potassium phosphate buffer pH 6.0, containing 2.0 g/l DL-α-N-hydroxyphenylglycine amide, was flushed with molecular nitrogen. Then 0.5 ml of Ochrobactrum cell suspension (50 mg dry weight per ml) was added to this reaction medium. This was again flushed with molecular nitrogen, and the incubation mixture was incubated at 40° C. with shaking (150 rpm). After 60 minutes 50% of the DL amide had been hydrolysed (HPLC analysis and ammonia determination). After 120 minutes and 180 minutes exactly the same concentrations of amide and ammonia were measured. An incubation with D- and L-α-N-hydroxyphenylglycine amide separately showed that only the L-amide had been hydrolysed.

Example VIII

The enantioselective hydrolysis of α-methylphenylglycine amide 2.0 ml of *Ochrobactrum anthropi* NCIB 40321 cell suspension (50 mg dry weight per ml) was added to 18 ml of 100 mM potassium phosphate buffer (pH 8.0) containing 2.0 g/l DL-α-methylphenylglycine amide. After 60 min. incubation (40° C., 150 rpm) 50% of the amide had been hydrolysed. Analysis of the remaining reaction mixture showed that both L-α-methylphenylglycine and D-α-methylphenylglycine amide were present with an e.e. of ≧99%.

Example IX

Enantioselective hydrolysis of valine amide

In the same way as in example VIII, an incubation was carried out with DL-valine amide. Analysis of the remaining reaction mixture after 4 hours showed that L-valine with an e.e. of 98.5% had been produced and that D-valine amide with an e.e. of 99% remained.

Example X

Enantioselective hydrolysis of α-methylvaline amide

In the same way as in example VIII, an incubation was carried out with DL-α-methylvaline amide. Analysis of the remaining reaction mixture after 8 hours showed that both L-α-methylvaline and D-α-methylvaline amide with an e.e. of ≧99.5% were present in the reaction mixture.

Example XI

Enantioselective hydrolysis of α-allyl-phenylglycineamide

In the same way as in example VIII, an incubation was carried out with DL-α-allyl-phenylglycine amide. Analysis of the remaining reaction mixture after 8 hours showed that L-α-allyl-phenylglycine with an e.e. of ≧99.5% had been produced and that D-α-allyl-phenylglycine amide with an e.e. of ≧99.5% remained.

Example XII

Enantioselective hydrolysis of α-propylphenylglycine amide

In the same way as in example VIII, an incubation was carried out with DL-α-propylphenylglycine amide. Analysis of the remaining reaction mixture after 8 hours showed that both L-α-propylphenylglycine and D-α-propylphenylglycine amide with an e.e. of ≧99.5% were present in the reaction mixture.

Example XIII

Enantioselective hydrolysis of α-ethylphenylglycineamide.

In the same way as in example VIII, an incubation was carried out with DL-α-ethylphenylglycine amide. Analysis of the remaining reaction mixture after 8 hours showed that both L-α-ethylphenylglycine and D-α-ethylphenylglycine amide with an e.e. of ≧99% were present in the reaction mixture.

Example XIV

Enantioselective hydrolysis of α-cinnamyl-alanine amide

In the same way as in example VIII, an incubation was carried out with DL-α-cinnamyl-alanine amide. Analysis of the remaining reaction mixture after 8 hours showed that both L-α-cinnamyl-alanine and D-α-cinnamyl-alanine amide with an e.e. of ≧99% were present in the reaction mixture.

Example XV

Enantioselective hydrolysis of tertiary leucine amide

In the same way as in example VIII, an incubation was carried out with DL-tertiary leucine amide. Analysis of the remaining reaction mixture after 8 hours showed that both L-tertiary leucine and D-tertiary leucine amide with an e.e. of ≧99% were present in the reaction mixture.

Example XVI

Enantioselective hydrolysis of α-methyl leucine amide

In the same way as in example VIII, an incubation was carried out with DL-α-methyl leucine amide. Analysis of the remaining reaction mixture after 4 hours showed that both L-α-methyl leucine and D-α-methyl leucine amide with an e.e of ≧99% were present in the reaction mixture.

We claim:

1. A process for the preparation of an L-carboxylic acid or a D-carboxylic acid amide comprising:
   selectively hydrolyzing a mixture D,L-carboxylic acid amides where the α-carbon has a substituent selected from the group consisting of an amino, a hydroxyl and an N-hydroxylamine with *Ochrobactrum anthropi* NCIB 40321 or a L-amidase derived therefrom, and
   recovering the L-carboxylic acid or the D-carboxylic acid amide.

2. The process according to claim 1 wherein the hydrolysis is carried out at a pH of between 4 and 9.5.

3. The process according to claim 1 wherein the hydrolysis is carried out at a temperature of between 30° and 70° C.

4. The process according to claim 1 wherein an α-amino acid amide is used as the substrate.

5. The process according to claim 4, wherein the α-amino acid amide is further substituted with an α-alkyl.

6. The process according to claim 1 wherein an α-N-hydroxyamino acid amide is used as the substrate.

7. The process according to claim 1 wherein an α-hydroxy acid amide is used as the substrate.

* * * * *